(12) United States Patent
Amagai et al.

(10) Patent No.: US 10,088,439 B2
(45) Date of Patent: Oct. 2, 2018

(54) THERMOPHYSICAL PROPERTY MEASUREMENT METHOD AND THERMOPHYSICAL PROPERTY MEASUREMENT APPARATUS

(71) Applicant: National Institute of Advanced Industrial Science and Technology, Tokyo (JP)

(72) Inventors: Yasutaka Amagai, Tsukuba (JP); Hiroyuki Fujiki, Tsukuba (JP); Nobuhisa Kaneko, Tsukuba (JP); Atsushi Yamamoto, Tsukuba (JP); Megumi Akoshima, Tsukuba (JP)

(73) Assignee: NATIONAL INSTITUTE OF ADVANCED INDUSTRIAL SCIENCE AND TECHNOLOGY (JP)

( * ) Notice: Subject to any disclaimer, the term of this patent is extended or adjusted under 35 U.S.C. 154(b) by 249 days.

(21) Appl. No.: 14/912,482

(22) PCT Filed: Jun. 6, 2014

(86) PCT No.: PCT/JP2014/065040
§ 371 (c)(1),
(2) Date: Feb. 17, 2016

(87) PCT Pub. No.: WO2015/025586
PCT Pub. Date: Feb. 26, 2015

(65) Prior Publication Data
US 2016/0202196 A1 Jul. 14, 2016

(30) Foreign Application Priority Data
Aug. 22, 2013 (JP) .................................. 2013-172318

(51) Int. Cl.
*G01N 25/18* (2006.01)
*G01K 13/00* (2006.01)
(Continued)

(52) U.S. Cl.
CPC ............... *G01N 25/18* (2013.01); *G01K 7/02* (2013.01); *G01K 13/00* (2013.01); *G01N 25/00* (2013.01)

(58) Field of Classification Search
None
See application file for complete search history.

(56) References Cited

U.S. PATENT DOCUMENTS

2009/0293928 A1  12/2009  Liang .......................... 136/201

FOREIGN PATENT DOCUMENTS

JP   01-161140    6/1989
JP   2003-014804  1/2003
(Continued)

OTHER PUBLICATIONS

Blatt et al. (Thermoelectric Power of Metals. Plenim Press, 1976, pp. 1-6 and 57-63).*

(Continued)

*Primary Examiner* — Christopher Mahoney
*Assistant Examiner* — Leon W Rhodes, Jr.
(74) *Attorney, Agent, or Firm* — Ostrolenk Faber LLP (57) ABSTRACT

Thermophysical property measurement apparatus and method that can obtain accurate absolute thermoelectric power and thermal conductivity are provided easily and conveniently. A thermophysical property measurement apparatus 50 is provided which includes a DC-AC voltage generator 100 which selectively applies AC or DC voltages of different polarities to a metal sample 4 to which temperature gradient is provided by connecting the metal sample 4 between metal blocks of temperatures $T_1$ and $T_2$; a thermocouple 5 which measures a temperature change at the center of the metal sample 4 when the AC voltage is applied thereto by the DC-AC voltage generator 100 and a temperature change at the center of the metal sample 4 when the DC (Continued)

voltages of the different polarities are applied; and an operation device 54 which calculates absolute thermoelectric power and thermal conductivity of the metal sample 4 using the two temperature changes measured by the thermocouple 5.

14 Claims, 3 Drawing Sheets

(51) Int. Cl.
*G01N 25/00* (2006.01)
*G01K 7/02* (2006.01)

(56) References Cited

FOREIGN PATENT DOCUMENTS

| JP | 2007-059462 | 3/2007 |
| JP | 2010-199343 | 9/2010 |
| JP | 2011-185697 | 9/2011 |

OTHER PUBLICATIONS

Sasaki et al, "A numerical simulation of thermoelectric effects in single-Junction thermal converters." IEEE Transactions on Instrumentation and Measurement, vol. 48, No. 2, 1999, pp. 408-411., doi:10.1109/19.769612.*

Harman, T. C., et al. "Measurement of Thermal Conductivity by Utilization of the Peltier Effect." Journal of Applied Physics, vol. 30, No. 9, 1959, pp. 1351-1359., doi:10.1063/1.1735334.*

Paul, "Simple apparatus for the multipurpose measurements of different thermoelectric parameters." Measurement, vol. 45, No. 1, 2012, pp. 133-139., doi:10.1016/j.measurement.2011.09.007.*

International Search Report dated Sep. 9, 2014 in corresponding PCT International Application No. PCT/JP2014/065040.

H.R. Nettleton "On the Measurement of the Thomson Effect in Wires," Proc. Phys. Soc. London, pp. 59-81 (1916).

R.B. Roberts, "The absolute scale of thermoelectricity," Philosophical Magazine, vol. 36, No. 1, pp. 91-107 (1977).

R.B. Roberts, "The absolute scale of thermoelectricity II," Philosophical Magazine Part B, vol. 43, No. 6, pp. 1125-1135 (1981).

R.B. Roberts et al., "The absolute scale of thermoelectricity III," Philosophical Magazine Part B, vol. 52, No. 6, pp. 1147-1163 (1985).

T. Nakamura et al., "Prototyping of AC method thermoelectric power measurement device," Proceedings of Academic Conference of the Japan Society of Applied Physics, JST document No. Y0055A, vol. 52, No. 1, p. 41 (1991), (with English translation).

A. Tamaki et al., "Prototyping of AC method thermoelectric measurement device and studies on thermoelectric power of rare-earth compounds," Annual Report, Research Institute for Technology, Tokyo Denki University, JST document No. L0877A, No. 10, p. 167-172 (1991), (English translation of Abstract).

Y. Amagai et al., "Study on Characterization of Thomson Coefficient Using AC Method toward the Absolute Scale of Thermoelectricity," 2013 Nen Dai 74 Kai The Japan Society of Applied Physics Autumn Meeting Koen Yokoshu, Aug. 31, 2013, 20p-C13-7, (see International Search Report).

M. Takimoto et al., "The Accurate Measurement of Absolute Thermoelectric Power," Extended Abstracts, Japan Society of Applied Physics and Related Societies 1997 Spring 1, The Japan Society of Applied Physics, Mar. 28, 1997, p. 66, (see International Search Report).

* cited by examiner

THERMOPHYSICAL PROPERTY MEASUREMENT METHOD AND THERMOPHYSICAL PROPERTY MEASUREMENT APPARATUS

CROSS-REFERENCE TO RELATED APPLICATIONS

The present application is a 35 U.S.C. §§ 371 national phase conversion of PCT/JP2014/065040, filed Jun. 6, 2014, which claims priority to Japanese Patent Application No. 2013-172318, filed Aug. 22, 2013, the contents of which are incorporated herein by reference. The PCT International Application was published in the Japanese language.

TECHNICAL FIELD

The present invention relates to methods and apparatuses for measuring thermophysical property values such as thermoelectric power and thermal conductivity of solids.

BACKGROUND ART

The absolute value of thermoelectric power of a metal material such as lead, platinum, etc., is a physical property value which is indispensable for a relative measurement method of thermoelectric power that is widely used in the field of physical property measurement. Absolute thermoelectric power is derived by comparative measurement with a superconductor as a reference material, using the fact that the Seebeck coefficient is zero in the superconducting state. This method causes a measurable temperature region to be restricted to a temperature which is lower than the superconducting transition temperature, so that it is necessary to derive the absolute thermoelectric power using the Kelvin relation from the measurable Thomson coefficient to expand the temperature measurement region.

Here, thermoelectric power S is generally defined as $S=\Delta V/\Delta T$ using a voltage $\Delta V$ which is produced when a temperature difference $\Delta T$ is imparted to a metal or a semiconductor. A measurement value of the thermoelectric power based on this definition more accurately applies to a relative value, or, in other words, a difference in the thermoelectric power of a metal to be measured and a wiring material (metal), so that a correction which takes into account the thermoelectric power of the wiring material is needed to determine the absolute thermoelectric power of the metal to be measured. More specifically, when the thermoelectric power of the metal to be measured is around several tens of $\mu$ V/K, an effect of such a correction cannot be neglected.

Now, while a number of devices for measuring the thermoelectric power have already been commercially available, a simple and convenient relative measurement method is adopted as the measurement principle in any one of the devices. Here, while, with the relative measurement method, it is necessary to correct a value of the thermoelectric power of the metal to be measured by measuring the absolute thermoelectric power of the wiring material included in the device, there are currently no facilities for actually measuring the absolute thermoelectric power, so that, as shown in NON-PATENT DOCUMENTS 2-4, in reality, each manufacturer depends on data on measurements of the absolute thermoelectric power that were carried out between the 1970's and the 1980's.

More specifically, ever since Nettleton proposed, in 1916, a method of calculating the Thomson coefficient when a polarity-inverted DC voltage is applied to a thin metal wire (below called "a DC inversion method") (see NON-PATENT DOCUMENT 1), the absolute thermoelectric power has been measured on lead, copper, platinum, etc., and determined for 0 to 1600 Kelvin (K) by Robert et al., (see NON-PATENT DOCUMENTS 2-4). Then, these measurement results have been widely adopted as reference values up to the present.

Here, the above-described Thomson coefficient $\mu$ is shown with the following Equation (1):

$$\mu = \frac{4\kappa a \delta T}{(T_2 - T_1)IL} \quad (1)$$

In the above Equation, $T_1$ and $T_2$ are temperatures in units of K at both ends of the metal to be measured when a voltage is applied to the both ends; I is a current in units of A, flowing through the metal; L is a length in m from an end to a midpoint of the metal; $\kappa$ is a thermal conductivity in units of W/mK of the metal; a is a cross-sectional area in units of $m^2$ of the metal; and $\delta T$ represents a half of a temperature change in units of K at the center (the midpoint) of the metal when a polarity-inverted DC current is passed through the metal to be measured.

Then, the absolute thermoelectric power S is calculated with the Kelvin equation, or Equation (2) below:

$$S = S(T_0) + \int_{T_0}^{T} \frac{\mu(T)}{T} dT \quad (2)$$

In the above Equation, $T_0$ means 92K, which is the superconducting transition temperature.

Moreover, from Equation (2), it is seen that the Thomson coefficient $\mu$ needs to be correctly determined to accurately determine the absolute thermoelectric power S.

Here, while a related-art absolute thermoelectric power measurement method determines the Thomson coefficient by measuring a temperature change caused by applying a DC voltage to a metal to be measured to which a temperature gradient is provided, a heat generation amount caused by the Thomson effect has a small value of less than or equal to approximately 1/100 of the Joule heat, which is generated at the same time.

Now, to perform accurate measurement of the heat amount, the above-described DC inversion method is being adopted in which the polarity-inverted DC current is passed through a subject to cancel out an effect of the Joule heat, which is generated by the current.

Now, the below-mentioned PATENT DOCUMENT 1 discloses a thermoelectric material evaluation device and a thermoelectric property evaluation method that calculate a thermoelectric power based on the above definition ($\Delta V/\Delta T$) of the absolute thermoelectric power S.

Moreover, the Thomson coefficient derivation equation (Nettleton's equation) is derived by the DC method based on the heat conduction equations in the below-mentioned NON-PATENT DOCUMENT 1, while the Nettleton's equation is used to actually measure, for the first time, the Seebeck coefficient from the Thomson coefficient for lead metal in NON-PATENT DOCUMENT 2.

Furthermore, the Seebeck coefficient is actually measured, for the first time, from the Thomson coefficient for copper metal by the current injection method in Non-patent document 3, while the Seebeck coefficient is actually measured, for the first time, in the range of 900K to 1600K from the Thomson coefficient for platinum metal by the current injection method in Non-patent document 4.

Moreover, non-patent documents 5 and 6 disclose a thermoelectric power measurement apparatus in which an AC method is adopted. Both relate to a method of measuring the thermoelectric power in a relative manner.

CITATION LIST

[PATENT DOCUMENT 1] JP2011-185697A
[NON-PATENT DOCUMENT 1] H. R. Nettleton, "On the measurement of the Thomson effect in wires", Proc. Phys. Soc. London (1916)
[NON-PATENT DOCUMENT 2] R. B. Robert, "The absolute scale of thermoelectricity", Philosophical Magazine, vol. 36, no. 1, pp. 91-107 (1977)
[NON-PATENT DOCUMENT 3] R. B. Robert, "The absolute scale of thermoelectricity", Philosophical Magazine Part B, vol. 43, no. 6, pp. 1125-1135 (1981)
[NON-PATENT DOCUMENT 4] R. B. Robert et al., "The absolute scale of thermoelectricity III", Philosophical Magazine Part B, vol. 52, no. 6, pp. 1147-1163 (1985)
[NON-PATENT DOCUMENT 5] Takashi Nakamura, Akira Tamaki, Tomoyoshi Aono, "Prototyping of AC method thermoelectric power measurement device", Proceedings of Academic Conference of the Japan Society of Applied Physics, JST document number Y0055A, vol. 52, no. 1, p. 41 (1991.10)
[NON-PATENT DOCUMENT 6] Akira Tamaki, Tomoyoshi Aono, "AC method thermoelectric measurement device and studies on thermoelectric power of rare-earth compounds", Annual Report, Research Institute for Technology, Tokyo Denki University, JST document number Y0877A, no. 10, p. 167-172 (1991.5)

DISCLOSURE OF THE INVENTION

Technical Problem

While any one of the physical quantities that make up Equation (1) can be measured, there is a problem that accurate measurements are difficult for the thermal conductivity κ or the length L of the metal to be measured. Moreover, while the current injection method has been devised in which the magnitude of current which is caused to flow such that the temperature of a predetermined portion of the metal to be measured is held constant is controlled, there is a problem that a complicated balancing operation is required since it is a type of non-balanced method, causing high skills to be needed.

Thus, most studies target relative thermoelectric power and no sufficient validations have been conducted for absolute thermoelectric power. Then, in actuality, a discrepancy between previous data obtained prior to 1970 and data measured again is also reported by the authors of NON-PATENT DOCUMENT 2 and there is a problem that a method of evaluating the absolute thermoelectric power has not yet been adequately established.

To solve the above-described problems, an object of the present invention is to provide a thermophysical property measurement method and a thermophysical property measurement apparatus that make it possible to simply and conveniently obtain accurate absolute thermoelectric power and thermal conductivity.

Technical Solution

To solve the above-described problems, a scheme is provided of applying an AC voltage or an AC current to a conductor or a semiconductor to which a temperature gradient is provided to measure a first temperature change of the conductor or the semiconductor; applying DC voltages or DC currents of different polarities to the conductor or the semiconductor to measure a second temperature change of the conductor or the semiconductor; and calculating at least one of an absolute thermoelectric power and a thermal conductivity of the conductor or the semiconductor using the measured first and second temperature changes.

Effects of the Invention

The present invention makes it possible to simply and conveniently obtain accurate absolute thermoelectric power and thermal conductivity.

MODE FOR CARRYING OUT THE INVENTION

First, the Thomson coefficient used in carrying out a thermophysical measurement method according to an embodiment of the present invention is described.

The present Thomson coefficient may be derived as follows, assuming that the alternating current-direct current (AC-DC) method, in which application of an alternating current voltage is combined with the direct-current (DC) inversion method, is used.

When an AC voltage $V_{AC}$ is applied to a metal to be measured (a thin metal wire) which meets thermal boundary conditions in the same manner as a case of applying a DC voltage to cause an AC current $I(\omega)$ to flow through the thin metal wire, the temperature distribution T in the steady state of the thin metal wire is shown with the heat conduction equation of Equation (3):

$$a\kappa \frac{\partial^2 T}{\partial x^2} - \mu I(\omega) \frac{\partial T}{\partial x} + \frac{I(\omega)^2 \rho}{a} = sd \frac{\partial T}{\partial t} \quad (3)$$

In the above Equation, x is a one-dimensional coordinate in units of length m, having one end of the thin metal wire as the origin; μ is the Thomson coefficient in units of μV/K; I(ω) is the current which flows through the thin metal wire in units of A; ρ is the electrical resistivity of the thin metal wire in units of Ω/m; s is the heat capacity of the thin metal wire in units of J/gK; d is the mass density of the thin metal wire in units of kg/m³; and t is time in units of seconds.

Here, as a time-varying sinusoidal AC voltage $V_{AC}$ is applied unlike for the direct current, the temperature is a function of time and location, so that partial differential equations need to be solved. While it is generally not simple to solve these heat conduction equations since they include variables in coefficients, it is relatively simple to determine an exact solution when the frequency is sufficiently high.

In other words, effects of heat absorption and heat generation that are caused by the Thomson effect are proportional to the sinusoidal current, so that, with the condition in which the frequency is sufficiently high ($\omega \gg \kappa/sdL^2$), contributions of the heat absorption and the heat generation by the Thomson effect are cancelled out. According to numerical simulations in the frequency region, a sufficient cancelling-out effect is obtained for 1 Hz or above depending on the dimension of the thin metal wire. Moreover, sufficient thermal averaging is obtained, so that the heat generation caused by the Joule effect may also be assumed to be constant. At this frequency limit, Equation (3) may be simplified as Equation (4):

$$\frac{d^2 T}{dx^2} - \frac{I^2 \rho}{a^2 \kappa} = 0 \qquad (4)$$

Then, a solution which meets the differential equation is determined to obtain Equation (5) as follows:

$$T_{AC} = \frac{DL^2}{2} + \frac{T_1 + T_2}{2} \qquad (5)$$

In the above Equation, the temperature $T_{AC}$ represents the temperature in units of K at the center of thin metal wire when the AC voltage $V_{AC}$ is applied thereto and D represents a coefficient for the Joule term.

In Equation (5), the first term corresponds to a temperature rise caused by the Joule heat generation and the second term corresponds to the initial temperature at the center of the thin metal wire with the temperature gradient provided to the thin metal wire. In other words, under the condition in which the frequency of the AC voltage applied is sufficiently high, the temperature distribution is such that the Thomson effect is canceled out and the temperature increase due to the Joule effect is just superimposed on the temperature gradient provided initially. Here, the temperature change $\Delta T_{AC}$ when the AC voltage is applied is defined as in the following Equation (6):

$$\Delta T_{AC} = \frac{DL^2}{2} \qquad (6)$$

As described below, when the initial temperature $(T_1 + T_2)/2$ is measured in advance by a thermocouple, etc., this amount may be obtained experimentally by subtracting the above-mentioned temperature from the temperature at the time of applying the current.

In this way, the temperature change $\delta T$, or, in other words, a half of the temperature change in units of K at the midpoint of the thin metal wire when the polarity-inverted DC current is passed through the thin metal wire as in the above $$\delta T = \frac{\Delta T_{AC} \cdot \mu}{\frac{2\rho L}{a} \cdot I}(T_1 - T_2) \qquad (7)$$

Here, the denominator of Equation (7) is the product of the current I and the electrical resistance R ($=2 \rho L/a$) of the thin metal wire, corresponding to the DC voltage $V_{DC}$, which is applied to the thin metal wire. In other words, the temperature difference caused by the Thomson effect shows that it is also proportional to the temperature gradient caused by the Joule effect in addition to the temperature gradient provided initially. Moreover, the larger the resistance of the thin metal wire, the smaller the temperature difference.

In the AC-DC method, as an AC voltage $V_{AC}$ whose effective value is equal to that of a DC voltage $V_{DC}$ is used, the above DC voltage $V_{DC}$ may be denoted as the AC voltage $V_{AC}$, so that the latter is used for the notation.

In this way, when the AC voltage $V_{AC}$, and the temperature change $\Delta T_{AC}$ of the thin metal wire when the AC voltage $V_{AC}$ is applied thereto are substituted into Equation (7) to solve for the Thomson coefficient $\mu$ on the right hand, the Thomson coefficient calculation equation may be obtained as follows:

$$\mu = \frac{V_{AC}}{(T_1 - T_2)} \cdot \frac{\delta T}{\Delta T_{AC}} \qquad (8)$$

When Equation (8) is compared to Equation (1) derived by Nettleton, while values of the AC voltage $V_{AC}$ and the temperature increase $\Delta T_{AC}$ of the thin metal wire when the AC voltage $V_{AC}$ is applied are needed, information on the geometric shape and the thermal conductivity of the thin metal wire that are difficult to measure accurately is not needed, so it is seen that the Thomson coefficient $\mu$ may be determined in principle.

Below, a thermophysical property measurement device and a thermophysical property measurement method for obtaining the Thomson coefficient using Equation (8), which is derived in this manner, are described in detail. The same letters in the present specification represent identical or similar parts.

Figure 1:
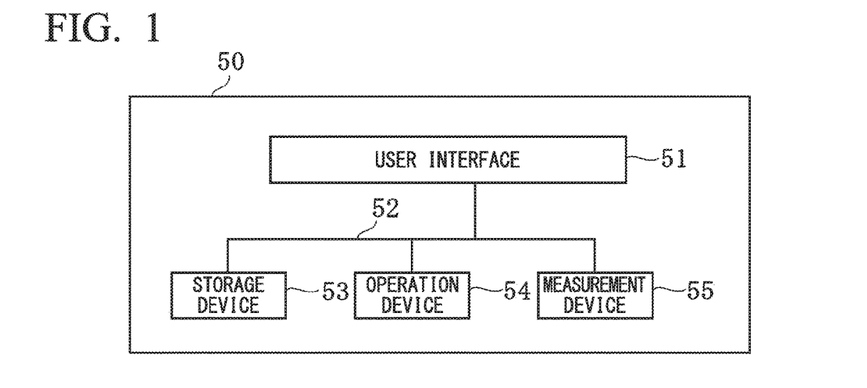
FIG. 1 is a block diagram illustrating the configuration of a thermophysical property measurement device 50 according to an embodiment of the present invention.

FIG. 1 is a block diagram showing the configuration of a thermophysical property measurement device 50 according to an embodiment of the present invention. As shown in FIG. 1, the thermophysical property measurement device 50 includes a user interface 51; a storage device 53; an operation device 54; a measurement device 55; and a bus 52 which connects therebetween.

Here, the user interface 51 has functions of accepting operation instructions of a user for the thermophysical property measurement device 50 and displaying generated data for the user to be able to recognize by visual inspection. Moreover, the storage device 53 stores programs executed by the operation device 54 and also stores data supplied via the bus 52. Moreover, the operation device 54 performs a predetermined operation on the supplied data by executing the programs stored in advance in the storage device 53. Then, as described in detail below, the measurement device 55 measures the thermoelectric properties included in the thin metal wire (below called "a metal sample"), etc.

Figure 2:
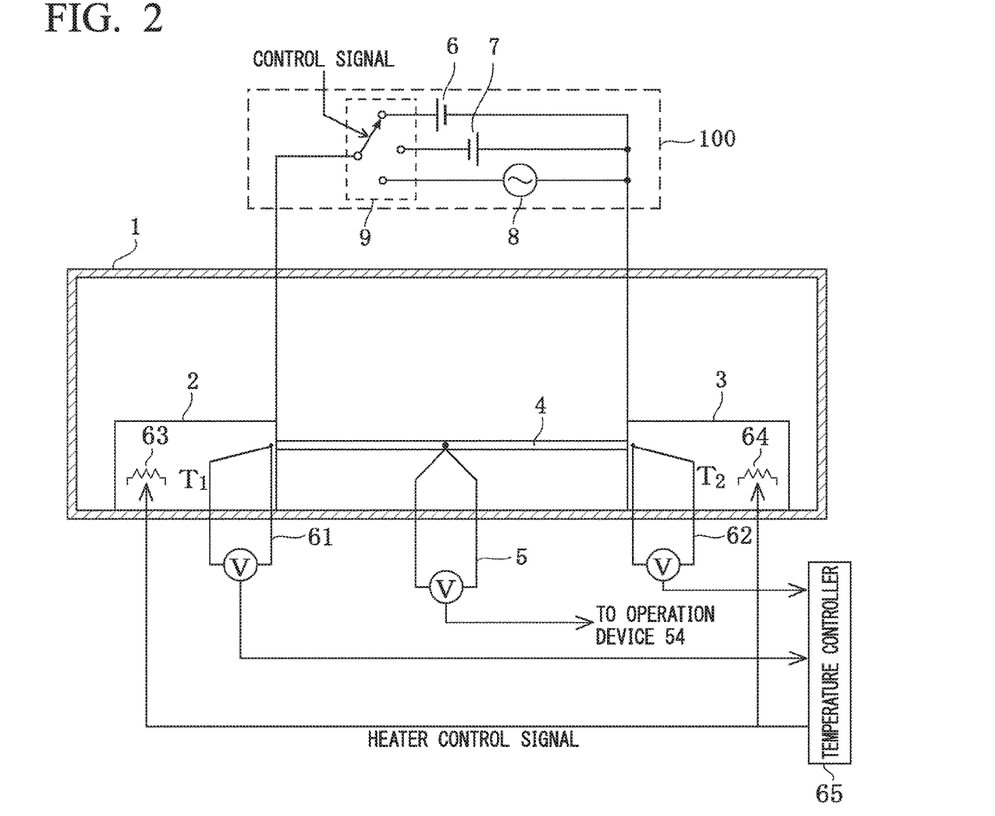
FIG. 2 is a diagram illustrating the configuration of a measurement device 55 shown in FIG. 1.

FIG. 2 is a diagram showing the configuration of the measurement device 55 shown in FIG. 1. As shown in FIG. 2, the measurement device 55 includes a chamber 1; metal blocks 2, 3; thermocouples 5, 61, and 62; heaters for heating

63, 64; a temperature controller 65; and a voltage application device 100. The voltage application device 100 includes a positive-polarity DC power supply 6; a negative-polarity DC power supply 7; an AC power supply 8; and a switch 9. Here, while a quantized AC voltage generator which can simply calculate the effective value may be used, for example, other power supplies may be used as the AC power supply 8.

Moreover, as shown in FIG. 2, the measurement point of the thermocouple 61 for measuring the temperature of the metal block 2 and the thermocouple 62 for measuring the temperature of the metal block 3 are respectively arranged at portions at which a metal sample 4 and the metal blocks 2 and 3 are connected. Then, the temperature controller 65 supplies a heater control signal in accordance with the temperature measured in the thermocouples 61 and 62 to control the heaters for heating 63 and 64 to supply the heat amount such that the temperature of the metal block 2 and the temperature of the metal block 3 are respectively brought to $T_1$ and $T_2$.

Then, the metal sample 4, for example, is installed in the measurement device 55, which has the configuration as described above, as a subject to be measured.

Here, the measurement device 55 is designed such as to be able to sufficiently satisfy thermal boundary conditions in thermal analysis. More specifically, the interior of the chamber 1 is made to be a vacuum to suppress heat convection, while the metal blocks 2 and 3 of temperatures $T_1$ and $T_2$ are connected to the metal sample 4 to provide a temperature gradient thereto as described above at each end of the metal sample 4. These metal blocks 2 and 3 have the function of a heat bath and the temperature is monitored with the thermocouples 61 and 62 while using a Peltier element, etc., making it possible to realize an accurate temperature control.

It is possible to use a tubular furnace which makes ambience control possible as well as to use a stable heater as a method of providing the temperature gradient to the metal sample 4.

Moreover, at the center of the metal sample 4, the thermocouple 5 is mounted to measure the heat absorption and the heat generation that are caused by the Thomson effect as well as the heat generation caused by the Joule effect when an AC voltage is applied. Here, to reduce outflow of heat from the thermocouple 5, a thermocouple whose thermal conductance is sufficiently small at less than or equal to 100 μm is mounted and an output voltage from the thermocouple 5 is measured by a nanovolt DC voltmeter. The temperature may possibly be measured by using a radiation thermometer in a region of high temperature of more than or equal to 900K.

Moreover, between both ends of the metal sample 4, a DC-AC voltage generator 100 which makes it possible to generate DC voltages of different polarities and AC voltages whose effective values are equal to those thereof. Here, it suffices for the waveform of the alternating current generated by the AC power supply 8 to be periodic, which may be a sinusoidal wave, a rectangular wave, etc., for example. Here, the optimum frequency is closely associated with a thermal time constant of the metal sample 4 and differs in accordance with the dimension, material, etc., of the metal sample 4, so that it is necessary to determine the optimum frequency upon conducting an experiment.

Moreover, to suppress generation of an error caused by a temporal change (drift) of a reference voltage of the DC-AC voltage generator 100, the switch 9 turns on, in order, the AC power supply 8, the positive-polarity DC power supply 6, the negative-polarity DC power supply 7, and the AC power supply 8, an operation of which is to be described later in detail.

Figure 3:
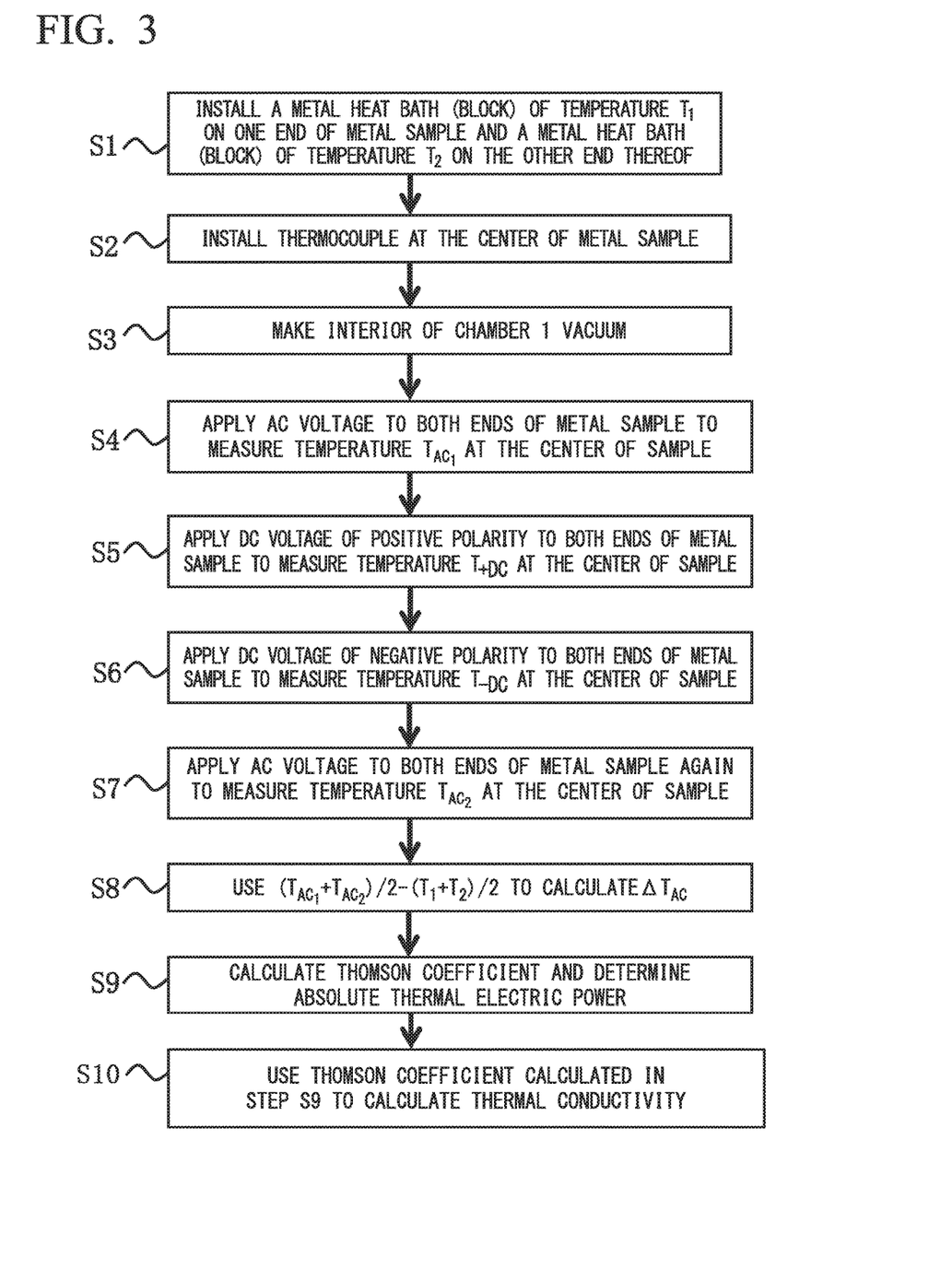
FIG. 3 is a flowchart for explaining a thermophysical property measurement method using the thermophysical property measurement device 50 shown in FIG. 1.

FIG. 3 is a flowchart for explaining a thermoelectric power measurement method which is realized by the thermophysical property measurement device 50 shown in FIG. 1. Hereinbelow, the thermoelectric power measurement method is described in detail using FIG. 3.

First, in step S1, the metal block 2 of temperature $T_1$ and the metal block 3 of temperature $T_2$ are installed on the respective ends of the metal sample 4. Next, in step S2, the thermocouple 5 is installed at the center of the metal sample 4 and, in step S3, the interior of the chamber 1 is made vacuum.

Then, in step S4, an AC voltage $V_{AC}$ is applied to both ends of the metal sample 4 to measure the temperature $T_{AC1}$ at the center of the metal sample 4 with the thermocouple 5.

Next, in step S5, a positive-polarity DC voltage $V_{+DC}$ is applied to both ends of the metal sample 4 to measure the temperature $T_{+DC}$ at the center of the metal sample 4 with the thermocouple 5.

Then, in step S6, a negative-polarity DC voltage $V_{-DC}$ is applied to both ends of the metal sample 4 to measure the temperature $T_{-DC}$ at the center of the metal sample 4 with the thermocouple 5.

Figure 4:
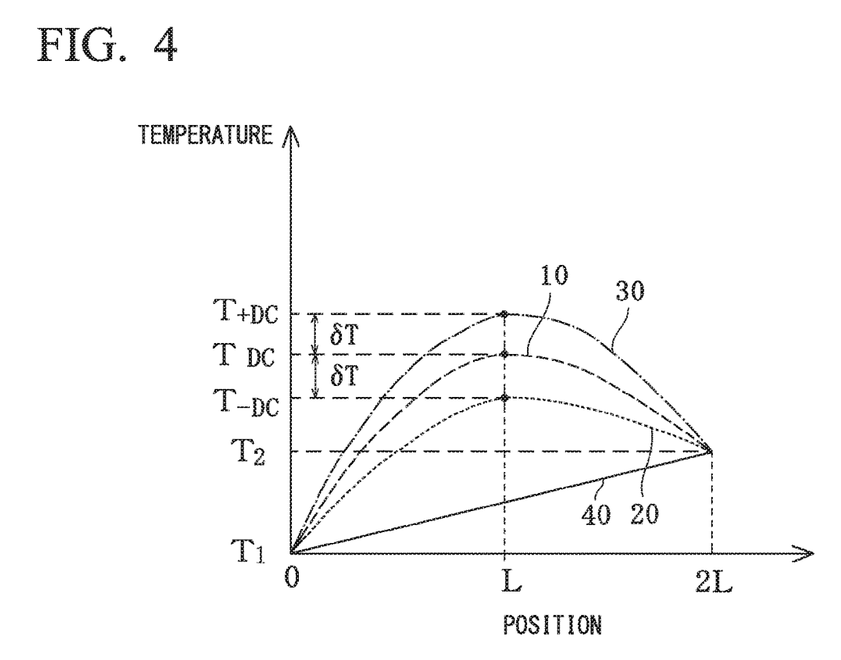
FIG. 4 is a graph illustrating the temperature distribution of a metal sample 4 when a DC voltage is applied thereto.

FIG. 4 is a graph showing the temperature distribution of the metal sample 4 when the DC voltage is applied. Here, the horizontal axis is the distance (position) from one end of the metal sample 4, while the vertical axis shows the temperature. As described above, the metal block 2 of the temperature $T_1$ is placed at one end of the metal sample of length 2L and the metal block 3 of the temperature $T_2$ is placed at the other end of the metal sample of length 2L, so that, as shown in a graph 40, the metal sample 4 has a temperature gradient which is in a fixed proportional relationship with the distance from one end between the temperatures $T_1$ and $T_2$ in the initial state. Thus, it is seen that the initial temperature $T_s$ at the midpoint (position L) of the metal sample 4 is $(T_1+T_2)/2$.

Then, as described above, the temperature distribution of the metal sample 4 when the positive-polarity DC voltage $V_{+DC}$ is applied to both ends of the metal sample 4 in step S5 is shown in a graph 30, while the temperature distribution of the metal sample 4 when the negative-polarity DC voltage $V_{-DC}$ is applied to both ends of the metal sample 4 in step S6 in a graph 20. Then, by passing the polarity-inversed current as described above, an effect of the Joule heat generated by the current is cancelled out, so that the temperature distribution of the metal sample 4 when there is no such effect as described above is shown with a graph 10, which is positioned between the graph 20 and the graph 30. Thus, when the DC voltage is applied to the metal sample 4, the temperature $T_{DC}$ at the midpoint when the effect caused by the current is filtered out may be evaluated as $(T_{+DC}+T_{-DC})/2$. Here, the operation device 54 shown in FIG. 1 computes ½ of the difference between the temperature $T_{+DC}$ and the temperature $T_{-DC}$ to calculate the temperature change δT.

Next, the AC voltage $V_{AC}$ is again applied to both ends of the metal sample 4 in step S7 to measure the temperature $T_{AC2}$ at the center of the metal sample 4 with the thermocouple 5.

Then, in step S8, the operation device 54 takes the difference between the temperature $(T_{AC1}+T_{AC2})/2$ and the initial temperature Ts to calculate the temperature change $\Delta T_{AC}$.

Figure 5:
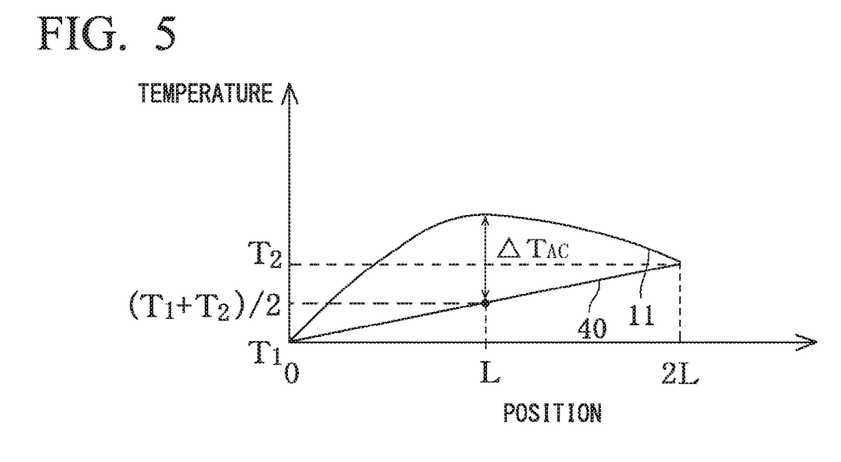
FIG. 5 is a graph illustrating the temperature distribution of the metal sample 4 when an AC voltage is applied thereto.

Here, FIG. 5 shows the graph 11 which shows the temperature distribution of the metal sample 4 when the AC voltage $V_{AC}$ is applied. In FIG. 5, in a similar manner to FIG. 4, the horizontal axis shows the distance (position) from one end of the metal sample 4, the vertical axis shows the temperature, and the temperature gradient in the initial state of the metal sample 4 is shown in the graph 40.

The graph 11 shows an average value of the temperature distribution of the metal sample 4 when the AC voltage $V_{AC}$ is applied in steps S4 and S7, and, as shown in FIG. 5, the temperature change $\Delta T_{AC}$ is shown as the difference between the graph 11 and the graph 40 at the midpoint of the metal sample 4.

Next, in step S9, the operation device 54 executes programs stored in advance in the storage device 53 to calculate the Thomson coefficient by Equation (8) using the obtained temperature change δ T and temperature change $\Delta T_{AC}$ and calculate the absolute thermoelectric power of the metal sample 4 by Equation (2) using the calculated Thomson coefficient.

Next, in step S10, the operation device 54 calculates the thermal conductivity as follows using the Thomson coefficient calculated in step S9.

Equation (1) is solved for the thermal conductivity κ to obtain Equation (9) as follows:

$$\kappa = \frac{IL(T_2 - T_1)}{4a\delta T}\mu \qquad (9)$$

Thus, the Thomson coefficient obtained in step S9 may be substituted into the right hand of Equation (9) to calculate the thermal conductivity of the metal sample 4. Here, there is a problem that, while the value of heat amount added is generally needed to calculate the thermal conductivity, it is difficult to accurately measure such a heat amount, so that it is not simple to obtain a highly accurate value. On the contrary, the above-described method may calculate the thermal conductivity using only the physical quantity which may be simply calculated, such as the temperature change at the center (midpoint) of the sample to be measured.

The values of the absolute thermoelectric power and the thermal conductivity that are calculated as described above are stored in the storage device 53 and the user interface 51 displays such values for the user of the thermophysical measurement device 50 to be able to recognize by visual inspection in accordance with predetermined operations instructions input by the user.

Moreover, the above-described thermoelectric power measurement method may achieve the same operational effects even when the subject to be measured is a metal, a semiconductor or a semimetal.

As described above, a thermoelectric measurement method and a thermoelectric measurement device according to embodiments of the present invention may accurately determine the Thomson coefficient μ using a simple scheme to easily and conveniently obtain accurate values of the absolute thermoelectric power and the thermal conductivity.

Then, accurate values of absolute thermoelectric power and thermal conductivity may be obtained to improve the accuracy and the reliability of existing thermophysical measurement devices and calculate values of thermoelectric power and thermal conductivity of new materials to achieve enhancement in the functionality of the existing thermophysical measurement devices, including the ability to realize a thermophysical property measurement device whose measurable temperature range is wider than that in the related art.

EXPLANATIONS OF REFERENCE 2, 3 Metal blocks
4 Thin metal wire (Metal sample)
5, 61, 62 thermocouples
6 Positive-polarity DC power supply
7 Negative-polarity DC power supply
8 AC power supply
9 Switch
50 Thermophysical property measurement device
54 Operation device
55 Measurement device
63, 64 Heaters for heating
65 Temperature controller
100 DC/AC voltage generator

The invention claimed is:

1. A thermophysical property measurement method, comprising:
    a first step of applying an AC voltage or an AC current to a metal to which a temperature gradient is provided to measure a first temperature change of the metal;
    a second step of applying DC voltages or DC currents of different polarities to the metal to measure a second temperature change of the metal; and
    a third step of calculating at least one of an absolute thermoelectric power and a thermal conductivity of the metal using the first temperature change and the second temperature change that are measured in the first step and the second step.

2. The thermophysical property measurement method as claimed in claim 1,
    wherein, in the first step and the second step,
    the voltage or the current is applied to both ends of the metal and first and second temperatures are measured at a center of the metal.

3. The thermophysical property measurement method as claimed in claim 1,
    wherein the AC voltage applied in the first step has an effective value of the same magnitude as that of the DC voltage.

4. The thermophysical property measurement method as claimed in claim 1,
    wherein the second step includes
    a positive voltage application step of applying a positive-polarity DC voltage to the metal to measure a temperature of the metal;
    a negative voltage application step of applying a negative-polarity DC voltage to the metal to measure the temperature of the metal; and
    a temperature change calculation step of calculating a difference in the temperature of the metal that is measured in the respective steps of the positive voltage application step and the negative voltage application step to set the calculated difference to be a second temperature.

5. The thermophysical property measurement method as claimed in claim 1,
    wherein the second step is executed following the first step;
    the thermophysical property measurement method further including a fourth step of further applying an AC voltage to the metal following the second step to measure a temperature change of the metal; and a fifth step of calculating an average value of the temperature change measured in the first step and the fourth step to set the calculated average value to be the first temperature change.

6. The thermophysical property measurement method as claimed in claim 1, wherein the third step includes a Thomson coefficient calculation step of calculating a Thomson coefficient of the metal; and a thermophysical property calculation step of calculating at least one of the absolute thermoelectric power and the thermal conductivity of the metal using the Thomson coefficient calculated in the Thomson coefficient calculation step.

7. A thermophysical property measurement apparatus, comprising:

a voltage application device which selectively applies an AC voltage or a DC voltage of a positive polarity or a negative polarity to a metal to which a temperature gradient is provided;

a temperature measurement device which measures a first temperature change of the metal by the voltage application device when the AC voltage is applied by the voltage application device and a second temperature change of the metal when the DC voltage of the positive polarity or the negative polarity is applied; and a thermophysical property calculation device which calculates at least one of an absolute thermoelectric power or a thermal conductivity of the metal using the first temperature change and the second temperature change.

8. The thermophysical property measurement apparatus as claimed in claim 7, wherein the voltage application device includes a quantized AC voltage generator which generates the AC voltage.

9. The thermophysical property measurement apparatus as claimed in claim 7, wherein the device which calculates the thermoelectric power calculates a difference between a temperature of the metal that is measured by the temperature measurement device when the DC voltage of the positive polarity is applied and a temperature measured by the temperature measurement device when the DC voltage of the negative polarity is applied to set the calculated difference to be the second temperature change.

10. The thermophysical property measurement apparatus as claimed in claim 7, wherein the voltage application device applies a sinusoidal wave AC voltage to the metal as the AC voltage.

11. The thermophysical property measurement apparatus as claimed in claim 7, wherein the voltage application device applies a rectangular wave AC voltage to the metal as the AC voltage.

12. The thermophysical property measurement apparatus as claimed in claim 7, wherein the temperature measurement device includes a thermocouple or a radiation thermometer.

13. The thermophysical property measurement apparatus as claimed in claim 7, further comprising:

two metal blocks, one of which is connected to one end of the metal and the other of which is connected to the other end of the metal; and a temperature setting device which sets the two metal blocks to respectively different temperatures.

14. The thermophysical property measurement apparatus as claimed in claim 13, further comprising:

a thermocouple which measures a temperature of the two metal block blocks at a connecting portion with the metal, wherein the temperature setting device sets the temperature of the two metal block blocks in accordance with the temperature measured by the thermocouple.

* * * * *